United States Patent [19]

Zengel et al.

[11] 4,238,404
[45] Dec. 9, 1980

[54] PROCESS FOR THE PREPARATION OF ISOCYANATE DERIVATIVES OF ALIPHATIC, CYCLOALIPHATIC, AND ARALIPHATIC COMPOUNDS

[75] Inventors: Hans Zengel, Kleinwallstadt; Manfred Bergfeld, Erlenbach; Rainer Zielke, Erlenbach; Erich Klimesch, Erlenbach, all of Fed. Rep. of Germany

[73] Assignee: Akzona Incorporated, Asheville, N.C.

[21] Appl. No.: 40,375

[22] Filed: May 18, 1979

[30] Foreign Application Priority Data

Jun. 5, 1978 [DE] Fed. Rep. of Germany ....... 2824648

[51] Int. Cl.$^3$ ............................................. C07C 118/04
[52] U.S. Cl. ...................................260/453 P; 564/58; 564/61; 564/117; 564/118
[58] Field of Search ...................................... 260/453 P

[56] References Cited

U.S. PATENT DOCUMENTS 3,483,242   12/1969   Brownstein et al. ............. 260/453 P

*Primary Examiner*—Dolph H. Torrence
*Attorney, Agent, or Firm*—Francis W. Young; Robert F. Green

[57] ABSTRACT

A process for the preparation of derivatives of aliphatic, cycloaliphatic, and araliphatic compounds containing from 1 to 3 isocyanate groups bonded to from 1 to 3 secondary or tertiary carbon atoms, or a combination thereof, is disclosed. The process comprises reacting a compound of the formula $R-(CO-NHCl)_n$, wherein R represents an aliphatic, cycloaliphatic, or araliphatic radical, with a tertiary amine having a $pK_a$ greater than 7, at a temperature from about 20° to about 180° C., in an inert solvent, to form a compound of the formula $R-(N=C=O)_n$, wherein the isocyanate groups are bonded to secondary or tertiary carbon atoms.

5 Claims, No Drawings

PROCESS FOR THE PREPARATION OF ISOCYANATE DERIVATIVES OF ALIPHATIC, CYCLOALIPHATIC, AND ARALIPHATIC COMPOUNDS

BACKGROUND OF THE INVENTION

This invention relates to a process for the preparation of isocyanates.

It is known that the reaction of carboxyl amides with a hypohalide in an alkaline aqueous, or alkaline alcoholic medium will lead to the intermediate formation of an N-halogen amide and subsequently, through thermal degradation (Hofmann degradation), to an isocyanate. However, the foregoing synthesis is not suitable for the preparation of isocyantes, because the highly reactive isocyanates immediately continue to react, either with water to form an amine, or with alcohol to form a urethane. Additionally, part of the resulting isocyante reacts with unconverted N-halogen amide, to form a haloacyl urea.

U.S. Pat. No. 3,483,242 teaches a process by which one starts with an N-halogen amide and heats the same in a stream of inert gas to temperatures ranging between the melting point of the N-halogen amide and 400° C. The purpose of the stream of inert gas, the velocity of which is between 25 and 1000 centimeters per minute, is to dilute the mixture to such an extent that the reaction products cannot react with one another. In addition, the stream of inert gas moves the reaction products to a condenser, where they are condensed and separated. In order to increase the yield, the reaction is performed in a solvent, such as aliphatic and aromatic nitro compounds, aromatic hydrocarbons, tertiary amines, halogenated hydrocarbons, and glycol ethers, preferably aprotic solvents, and particularly chloroform.

In the aforementioned process, the use of a base is not considered necessary, but in some cases a base is indicated to bring about an increase in yield. Inorganic bases, such as sodium hydroxide, calcium oxide, sodium carbonate, or aluminum oxide, are exclusively recommended. The process may be performed above the melting poing of the halogen amide being used. However, since the halogen amides decompose below their melting point, with formation of undesirable by-products, the attainable isocyanate yields are low. With phenyl isocyanate the yield is a maximum of 39.9%, for benzyl isocyanate 8.6%, for para-methoxyphenyl isocyanate 17%, and for cyclohexyl isocyanate 30%, of theoretical.

The object of the present invention is thus to prepare numerous aliphatic, alkyl aromatic, and cycloaliphatic mono-, bis and tris-isocyanates with substantially higher yields than those obtainable with the processes of prior art.

SUMMARY OF THE INVENTION

There has now been discovered a process for the preparation of derivatives of aliphatic, cycloaliphatic, and araliphatic compounds containing 1 to 3 isocyanate groups bonded to from 1 to 3 secondary or tertiary carbon atoms. The process comprises reacting an aliphatic, cycloaliphatic, or araliphatic compound containing from 1 to 3 N-chloro amide groups bound to from 1 to 3 secondary or tertiary carbon atoms, or a combination thereof, with a tertiary amine having a $pK_a$ greater than 7, at a temperature from about 20 to about 180° C., in an inert solvent, to convert the N-chloro amide groups into isocyanate groups.

DESCRIPTION OF THE PREFERRED EMBODIMENTS

Utilizing the process of the present invention it is possible to prepare secondary aliphatic monoisocyantes, such as 1-methylpropane isocyante, 1-ethylpentane isocyanate, 1-methylbutane isocyanate, and isoheptadecane isocyanate. Furthermore, the process lends itself to the preparation of tertiary aliphatic monoisocyanates such as 1,1-dimethylethane isocyanate and 1,1-diethylpropane isocyanate, as well as secondary aliphatic isocyanates such as hexane-2,5-diisocyanate and heptane-2,6-diisocyanate. Furthermore, tertiary aliphatic diisocyanates such as 2,5-dimethylhexane-2,5-diisocyanate may also be prepared, and likewise secondary aliphatic triisocyanates such as 5-methylnonane-2,5,8-triisocyanate. Furthermore the process is capable of preparing tertiary aliphatic triisocyanates such as 2,5,8-trimethylnonane-2,5,8-triisocyanate. The aliphatic radicals of the mono-, di- and triisocyanates typically contain from 3 to 30 carbon atoms.

Furthermore, it is possible utilizing the process of the instant invention to prepare araliphatic mono-, di- and triisocyanates which have, as in the foregoing instance, the isocyanate groups linked to 1, 2, or 3 different secondary or tertiary carbon atoms, thus to the aliphatic part of the alkyl aromatic compound. In the case of the aromatic radicals of such compounds of which there may be several, aryl radicals with 6 to 18 carbon atoms are typically involved, particularly phenyl, naphthyl, anthracene, phenanthrene, pyrene and chrysene radicals. If necessary such radicals may be replaced by substituents which are inert with respect to isocyanates and N-chloramides, such as alkyl, halogen, nitro, alkoxy, phenyl and/or dialkylamino groups. The aliphatic radicals of such compounds likewise typically have from 3 to 30 carbon atoms. Examples of such compounds are 1-phenylpropane isocyanate, diphenylmethane isocyanate, 1-para-diphenylpropane isocyanate and 1-naphthylpropane isocyanate.

Also, cycloaliphatic mono-, di-, and triisocyanates are also accessible by means of the process pursuant to the present invention. Among the foregoing are cycloaliphatic mono-, di-, and triisocyanates in which the isocyanate groups are bonded directly to the secondary cyclic carbon atoms of the cycloaliphatic radical, for example cyclohexane isocyanates, the stereo-isomeric cyclohexane-1,4-diisocyanates and cyclohexane-1,3,5-triisocyanate. Cycloaliphatic radicals of such compounds may possess from 4 to 18 carbon atoms.

When selecting an organic solvent for use in the present process care must be taken that under the conditions of the reaction, it will not react with the N-chloramide or with the isocyanate or with the tertiary amine. Typical suitable solvents are: methylene chloride, 1,1-dichloroethylene, chloroform, carbon tetrachloride, trichloroethylene, tetrachloroethylene, pentane, hexane, cyclohexane, heptane, octane, benzene, toluene, ethyl benzene, chlorobenzene, xylene, dichlorobenzene, diethyl ether, tetrahydrofuran, dioxane, methyl acetate, butyl acetate, and methyl propionate. Preferable solvents are toluene, xylene, chlorobenzene, butyl acetate, chloroform, tetrachloroethylene, carbon tetrachloride, cyclohexane, and dioxane.

Selection of a suitable base is highly important to the success of the present process. The inorganic bases recommended in the known prior art processes cannot be used in the present process because in such instances water is formed during the reaction which immediately reacts with the isocyanate. Instead, pursuant to the present invention, one may utilize tertiary amines with a certain basicity. The basicity constant $pK_a$ is given as a measure of the basicity and tertiary amines suitable for the process of the present invention have a minimum basicity corresponding to a $pK_a$ value greater than 7. Suitable tertiary amines are aliphatic, cycloaliphatic, and aromatic amines, such as the following ($pK_a$ values at 25° C. being in parentheses): trimethyl amine (9.80), triethyl amine (10.74), tri-n-butyl amine (9.89), 2,4,6-trimethyl pyridine (7.45–7.63), tri-n-propyl amine (10.74), ethyldimethyl amine (10.06), propyldimethyl amine (10.16), isopropyldimethyl amine (10.38), methyldimethyl amine (10.43), butyldimethyl amine (10.31), 2,3,4,5-tetramethyl pyridine (7.78), and 2,3,4,5,6-pentamethyl pyridine (8.75). The preferred tertiary amines are trimethyl amine, triethyl amine, tri-n-propylamine and tri-n-butyl amine. The $pK_a$ values may be found in customary handbooks. In particular, so far as aliphatic tertiary amines are concerned, one may refer to L. Spialter et al, "The Acyclic Aliphatic Tertiary Amines", The McMillan Company, New York (1965), and with respect to substituted pyridines, to Klingsberg, Heterocyclic Compounds, Pyridine and Derivatives, part 2, Interscience Publishers, Inc., New York (1961).

The basicity of the tertiary amine is of particular importance with respect to the progress of the reaction in the sense that when the same N-chloramide is utilized, the isocyanate yield is lower, when the tertiary amine having a lower $pK_a$ value is utilized. For example, in the synthesis of 1,1-dimethyl isocyanate from 2,2-dimethylpropionic acid-N-chloramide the yield amounts to 86% in the case of triethyl amine ($pK_a$ at 25° C.=10.74), while with tri-n-butyl amine ($pK_a$ value at 25° C.=9.89) the yield is 77%. The yield with trimethyl amine ($pK_a$ value at 25° C.=9.80) it is 65.3% and with 2,4,6-trimethyl pyridine ($pK_a$ value at 25° C.=7.45–7.63) the yield is 38.0% of theoretical. When 4-methyl pyridine is utilized, the $pK_a$ value of which at 25° C. is only 6.02 to 6.11, the isocyanate yield under otherwise identical conditions is only 4.0% of theoretical.

In the process of the present invention, the reaction temperatures are within the range from about 20° to about 180° C. It is also possible to distill the isocyanate directly from the reaction mixture, without the preceding separation of the amine hydrochloride. Naturally, the isocyanate may also be extracted from the reaction mixture in different ways, as may be appropriate in the individual case, for example, extraction of the amine hydrochloride with water, followed by distillation of the solvent and isocyanate may be appropriate.

Compared with the known processes, the present process is distinguished, in particular, by high yields. Additional advantages include short reaction times and lower reaction temperatures. Also, substantial dilution of the reaction mixture by a stream of inert gas is not required.

The process of the present invention is explained in greater detail by means of the following examples. In some cases, the isocyanate was distilled over directly with the solvent and then, for an easier determination of the yield, immediately transformed into a urea.

EXAMPLE 1

6.78 g (0.05 mol) of 2-methylbutyric-N-chloramide (92.7%) and 100 g chlorobenzene were placed in a 250 ml threenecked flask equipped with stirrer, thermometer and fractionating column. Addition of 15.2 g (0.15 mol) triethyl amine immediately resulted in formation of a clear solution, which was placed in an oil bath preheated to 160° C. The reflux temperature (124° C.) was reached within 3 minutes and triethylamine hydrochloride precipitated. After boiling for 40 minutes at reflux the heating bath was removed, the liquid cooled to room temperature, drawn off from the triethylamine hydrochloride by suction and the filtrate distilled without vacuum. 7.3 g (0.1 mol) diethylamine were added to the distillate, which contained chlorobenzene, triethylamine and 1-methylpropane isocyanate and from which the volatile constituents were removed during one hour in a rotary evaporator. The residue consisted of 4.21 g N-1-methylpropyl-N'-diethyl urea, corresponding to 2.41 g of 1-methylpropane isocyanate isocyanate, which amounts to a yield of 53.0%, referred to the charged chloramide.

EXAMPLE 2

Example 2 was carried out completely analogous to Example 1, except that instead of chlorobenzene, use was made of the same quantity of toluene. 4.88 g of N-1-methylpropyl-N'-diethyl urea were obtained, which corresponds to a yield of 56.7% 1-methylpropane isocyanate, referred to the charged chloramide.

EXAMPLE 3

In the equipment described in Example 1, 6.78 g (0.05 mol) of 2,2-dimethylpropionic-N-chloramide (98%) were dissolved in 100 g toluene, 15.2 g (0.15 mol) triethylamine added thereto and the solution immediately heated to reflux (108° C.) in an oil bath preheated to 120° C.; precipitation of triethylamine hydrochloride began already at 40° C. A reaction time of 45 minutes was followed by cooling, separation of the precipitated triethylamine hydrochloride by suction and distillation at normal pressure of the yellowish-brown mother liquor (Bp=90° to 108° C., bath=130° to 140° C.). The distillate was mixed with 7.3 g (0.1 mol) diethylamine and, after 15 minutes, concentrated in a rotary evaporator. The residue consisted of 7.20 g N-1-dimethylethyl-N'-diethyl urea in the form of white crystals melting at 66°–67° C., which were identified by means of elementary analysis and IR spectroscopy. This corresponds to a yield of 86% of 1,1-dimethylethane isocyanate, referred to the charged chloramide.

EXAMPLE 4

In the equipment described in Example 1, 8.88 g (0.05 mol) of 2-ethylhexanoic-N-chloramide (95.7%) were dissolved in toluene, 15.2 g (0.15 mol) triethylamine added thereto and the solution immediately heated by placing it in an oil bath preheated to 130° C. Precipitation of triethylamine hydrochloride started at an internal temperature of 80° C.; first, boiling was continued for 30 minutes at reflux, after which 24 g of an amine/toluene mixture were distilled off within 30 minutes. This was followed by cooling to room temperature and removal of the precipitated triethylamine hydrochloride by suction. First the solvent was distilled off from the light brown filtrate under an operating vacuum ($17 \times 10^3$ Pa), then under a water-jet vacuum at Bp=66°–67° C., (1.95×10³ Pa) the 1-ethylpentane isocyanate in the form of a colorless liquid. The yield was 5.2 g, corresponding to 77%, referred to the charged chloramide.

EXAMPLE 5

In the equipment described in Example 1, 16.0 g (0.05 mol) of isooctadecanoic-N-chloramide (84%) were dissolved in 150 g chlorobenzene, and 15.2 g (0.15 mol) triethylamine added thereto. The solution was heated to reflux in an oil bath preheated to 170° C.; separation of triethylamine hydrochloride began at an internal temperature of 70° C. Boiling continued at reflux (internal temperature of 125° C.) for 30 minutes, after which 26 g of a triethylamine/chlorobenzene mixture were drawn off within additional minutes. After cooling, the triethylamine hydrochloride was separated by suction, the filtrate first freed of solvent under an operating vacuum (17×10³ Pa) and then the product itself distilled off under a pump vacuum at Bp=96°–105° C. (33 Pa) and a bath temperature of 140°–165° C. The result amounted to 9.9 g isoheptadecane isocyanate, corresponding to a yield of 84%, referred to the charged chloramide.

EXAMPLE 6

9.86 g (0.05 mol) of 2-phenylbutyric-N-chloramide (86.9%) were dispersed in 150 g chlorobenzene, in the same equipment as in the preceding examples, and 15.2 g (0.15 mol) added thereto, which resulted in a clear solution. During heating up in a preheated bath (160° C.), the triethylamine hydrochloride precipitated already at an internal temperature of 70° C. The mixture was boiled for 30 minutes at reflux (internal temperature=121° C.), after which 24 g of distillate were drawn off within 30 minutes. After cooling to room temperature, the triethylamine hydrochloride was separated by suction, the filtrate first freed from solvent in an operating vacuum (17×10³ Pa) and then the 1-phenylpropane isocyanate distilled off at Bp=42°–50° C. (33 Pa). The yield was 4.91 g, corresponding to 70% of the theory, referred to the chloramide.

EXAMPLE 7

12.3 g (0.05 mol) diphenylacetic-N-chloramide (98%) were suspended in 150 g chlorobenzene and 15.2 g (0.15 mol) added thereto. With heating to 30° C., a clear solution was formed immediately, which was brought to boiling in a preheated bath (160° C.). Already from an internal temperature of 70° C. on, triethylamine hydrochloride began to separate. Following boiling for one hour, in the course of which 16 g distillate were collected, the liquid was cooled, withdrawn by suction, and the filtrate distilled. At a Bp=103° to 105° C. (50 Pa), 4.1 g diphenylmethane isocyanate passed over; this corresponds to a yield of 40% referred to the chloramide.

EXAMPLE 8

16.2 g (0.1 mol) cyclohexanecarboxylic-N-chloramide (95%) were suspended in 250 ml chlorobenzene in the usual equipment, and 30.3 g (0.3 mol) triethylamine added thereto, which resulted in a clear solution. The latter was quickly heated by means of a bath preheated to 160° C. Precipitation started at an internal temperature of 65° C.; boiling was continued for a total of 1 hour, during which altogether 100 g of distillate were drawn off. After cooling, the triethylamine was separated by suction and the filtrate distilled under an operating vacuum at Bp=72°–104° C. (17×10³ Pa). The isocyanate content of the distillate was determined by means of titration; it amounted to 8.7 g, corresponding to a yield of 73%, referred to the chloramide.

EXAMPLE 9

Example 8 was repeated in exactly the same manner, except that the same quantity of toluene was used instead of the chlorobenzene. On this occasion, better extraction of the isocyanate by means of distillation was possible, producing 7.91 g, corresponding to a yield of 66.5%, referred to the chloramide, obtained at Bp=85°–87° C. (17×10³ Pa).

EXAMPLE 10

150 g of chlorobenzene and 30.3 g (0.3 mol) triethylamine were added to 12.5 g (0.05 mol) 2,5-dimethyladipic-di-N-chloramide in the equipment described in Example 1, and heated in a preheated bath (135° C.). Without preceding complete solution of the product, an exothermic reaction began at 95° C.; after boiling for 30 minutes at reflux, 15.9 g of distillate were withdrawn within another 30 minutes. After cooling, the triethylamine hydrochloride was separated by suction and the product distilled first under an operating vacuum, then under a pump vacuum, whereby 4.5 g hexane-2,5-diisocyanate of a Bp=57°–59° (70 Pa) were obtained. The yield was 62%, referred to the chloramide.

The isocyanate had the following analysis data:

|  | % C | % H | % N | % NCO |
| --- | --- | --- | --- | --- |
| found: | 57.4 | 7.4 | 17.2 | 48.4 |
| calculated: | 57.14 | 7.14 | 16.67 | 50.00 |

EXAMPLE 11

Example 10 was repeated in the same manner, except that the chlorobenzene was replaced by toluene. 4.5 g hexane-2,5-diisocyanate distilled over at Bp=52°–56° C. (50 Pa), which, referred to the chloramide, corresponds to a yield of 42%.

EXAMPLE 12

60 g (0.6 mol) triethylamine were added to a suspension of 23.9 g (0.1 mol) 1,4-cyclohexane dicarboxylic-N-chloramide (90%) in 200 ml chlorobenzene, which was rapidly preheated to 100° C.; subsequently, excess triethylamine and 50 ml chlorobenzene were distilled off. The precipitated triethylamine hydrochloride was separated at room temperature and chlorobenzene, as well as cyclohexane-1,4-diisocyanate distilled off. 10.2 g diisocyanate, corresponding to a yield of 68.3%, were obtained.

The reaction was carried out analogously, with toluene and o-xylene as reaction media. The results were diisocyanate yields of 55% (toluene) and 53% (o-xylene).

EXAMPLE 13

68 g (0.05 mol) 2,2-dimethylpropionic-N-chloramide (98%) were dissolved in 35 g toluene and a solution of 8.9 g (0.15 mol) trimethylamine in 65 g toluene added thereto, which was accompanied by heating to 30° C. The liquid was quickly heated to the reflux temperature (110° C.) by placing it in a bath preheated to 140° C. Trimethylamine hydrochloride began to precipitate already during heating up, and gaseous trimethylamine escaped through the reflux cooler. Boiling was continued for 1 hour, followed by cooling, separation of trimethylamine hydrochloride by suction, and distilling of the filtrate under normal pressure. 7.3 g (0.1 mol) diethylamine were added to the distillate, which, after standing for 30 minutes, was freed from the volatile constituents in a rotary evaporator. The resulting residue was 5.5 g N-1,1-dimethylethyl-1-n'-diethyl urea, corresponding to a yield of 65.3%, referred to the charged chloramide.

EXAMPLE 14

In the equipment described in Example 1, 9.86 g (0.05 mol) 2-phenylbutyric-N-chloramide (86.9%) were dispersed in 150 g chlorobenzene and 21.5 g (0.15 mol) tri-n-propylamine added thereto, whereupon a clear solution was immediately formed. After having been at reflux for 1 hour (internal temperature 130° C.), the clear solution was subjected to distillation, whereby 3.6 g 1-phenylpropane isocyanate went over last under a pump vacuum at Bp=50°-55° C. (40 Pa); referred to the chloramide, this corresponds to a yield of 52%.

EXAMPLE 15

6.8 g (0.05 mol) 2,2-dimethylpropionic-N-chloramide (98%) were dissolved in 100 g toluene, 27.8 g (0.15 mol) tri-n-butylamine added thereto, and quickly heated to boiling as in the preceding examples. After boiling for 1 hour (internal temperature 110° to 112° C.), all volatile substances were distilled off under an operating vacuum $(17 \times 10^3$ Pa) at Bp=56°-62° C. and the isocyanate content of the distillate determined by titration. After that, 7.3 g (0.1 mol) diethylamine were added and the solvent drawn off in a rotary evaporator after 30 minutes; the result was 6.6 g N-1,1-dimethylethyl-N'-diethyl urea which, referred to the chloramide, corresponds to an isocyanate yield of 77%.

EXAMPLE 16

6.8 g (0.05 mol) 2,2-dimethylpropionic-N-chloramide (98%) were dissolved in 100 g toluene, 18.2 g (0.15 mol) 2,4,6-trimethyl pyridine (collidine) added thereto, and the solution quickly heated to reflux (110° C.) by placing it in a bath preheated to 130° C.; 2,4,6-trimethyl pyridine hydrochloride precipitated after 10 minutes. The solution was heated for 1 hour at reflux, then cooled, and removed by suction from the precipitate. The filtrate was distilled under an operating vacuum $(17 \times 10^3$ Pa) at Bp=58°-62° C. and the distillate mixed with 7.3 g (0.1 mol) diethylamine. The solvent was drawn off after brief standing, resulting in 3.30 g N-1,1-dimethylethyl-N'-diethyl urea as residue; referred to the chloramide, this corresponds to a yield of 38%.

EXAMPLE 17

6.8 g (0.05 mol) 2,2-dimethylpropionic-N-chloramide (98%) were dissolved in 100 g chlorobenzene, 14.0 g (0.15 mol) 4-methylpyridine (4-picoline) added thereto, and the solution heated quickly. A strong discoloration quickly took place after the reflux temperature had been reached (130° C.), and a dark, tarry mass separated on the walls. Treatment for 1 hour was followed by cooling to room temperature, whereby golden yellow platelets formed; these, as well as the tarry mass were separated and the filtrate distilled under an operating vacuum $(17 \times 10^3$ Pa) at Bp=58°-62° C. As in Example 15, diethylamine was added to the distillate, which was processed; 0.35 g N-1,1-dimethylethyl-N'-diethyl urea, corresponding to an isocyanate yield of 4%, referred to the chloramide, was isolated.

EXAMPLE 18

Making use of the equipment described in Example 1, 9.86 g (0.05 mol) 2-phenylbutyric-N-chloramide were suspended in 100 g acetic butyl ester and 15.2 g (0.15 mol) triethylamine added thereto, whereby a clear solution was formed immediately; the solution warmed up even before placement into a bath preheated to 170° C. and triethylamine hydrochloride began to separate. Boiling at reflux (internal temperature 120° C.) for 30 minutes and withdrawal of 26 g of distillate within another 30 minutes was followed by cooling, withdrawal by suction and distillation of the filtrate. After the solvent, 3.5 g 1-phenylpropane isocyanate distilled over at Bp=50°-54° C.; referred to the charged chloramide, this corresponds to a yield of 50%.

EXAMPLE 19

9.86 g (0.05 mol) 2-phenylbutyric-N-chloramide (90%) were dispersed as usual, in 150 g carbon tetrachloride, and 15.2 g (0.15 mol) triethylamine added thereto; this resulted in partial solution of the chloramide. The mixture was quickly heated in a preheated with (120° C.) and boiled for 1 hour at reflux. After cooling, the formed triethylamine hydrochloride was separated by suction and the filtrate distilled, whereby 4.8 g 1-phenylpropane isocyanate went over at Bp=45°-55° C. (40 Pa), which corresponds to a yield of 66%, referred to the chloramide.

EXAMPLE 20

8.1 g (0.05 mol) 2-phenylbutyric-N-chloramide (90%) were dissolved in 100 g dioxane and 15.2 g (0.15 mol) triethylamine added thereto. A slight increase in temperature, and precipitation, occurred even before placement in the bath preheated to 135° C. Boiling at reflux was continued for 30 minutes at an internal temperature opf 98° C., after which 32 g of distillate were withdrawn within another 30 minutes. After cooling, the formed triethylamine hydrochloride was separated by suction, the filtered mother liquor first freed from solvent and the 1-phenylpropane isocyanate distilled off at Bp=45°-55° C. (40 Pa); referred to the chloramide, the yield of 3.83 g corresponded to 53.0%.

EXAMPLE 21

8.1 g (0.05 mol) cyclohexanecarboxylic-N-chloramide (95%) were added at room temperature to 72 g (0.7 mol) triethylamine, making use of the equipment described in Example 1, whereby, accompanied by heating to 40° C., most of it dissolved. Heating up was accomplished by placement in preheated bath (120° C.), followed by boiling for 30 minutes at reflux. A precipitate formed already during heating up, which was separated by suction after cooling. The filtrate was first distilled under an operating vacuum $(17 \times 10^3$ Pa), on which occasion 2.12 g cyclohexane isocyanate, corresponding to a yield of 36%, referred to the chloramide, went over at Bp=55°-57° C.

EXAMPLE 22

6.8 (0.05 mol) 2,2-dimethylpropionic-N-chloramide (98%) were put in a flask with stirrer and fractionating column and 9.25 g (0.05 mol) tri-n-butylamine added thereto. After a few minutes, the mixture heated up to 135° C. and, at Bp=85° C., 1,1-dimethylethane isocyanate distilled over under normal pressure. After the violent reaction has died down, additional isocyanate was distilled over by briefly heating the flask in an oil bath to 150° C. A total of 3.33 g of 1,1-dimethylethane isocyanate went over, which corresponds to a yield of 68%, referred to the chloramide.

EXAMPLE 23

The reaction was carried out analogous to Example 6, but with a reaction time of only 4 minutes and a reaction temperature of 105° C. The yield of 1-phenylpropane isocyanate amounted to 4.87 g, corresponding to 69.6% of the theory, referred to the chloramide.

EXAMPLE 24

9.86 g (0.05 mol) 2-phenylbutyric-N-chloramide (86.9%) were suspended in a mixture of 100 g tetrachloroethylene and 15.2 g (0.15 mol) triethylamine. After 30 minutes of heating at reflux, the cooled mixture was extracted with 50 ml of water in order to separate the triethylamine hydrochloride, and the organic phase distilled off after that. 4.65 g a-phenylpropane isocyanate, corresponding to a yield of 66.5%, referred to the chloramide, were obtained.

EXAMPLE 25

9.86 (0.05 mol) 2-phenylbutyric-N-chloramide (86.9%), together with 2 g (0.05 mol) pulverized sodium hydroxide, was suspended in 100 g toluene and heated for 30 minutes at reflux. After cooling, the insoluble constituents were removed and the filtrate distilled.

The yield of 1-phenylpropane isocyanate was 0.07 g, corresponding to 1% of the theory, referred to the chloramide.

What is claimed is:

1. A process comprising reacting an aliphatic, cycloaliphatic, or araliphatic compound containing from 1 to 3 N-chloramide groups bound to from 1 to 3 secondary or tertiary carbon atoms which are part of (1) an aliphatic radical which contains from 3 to 30 carbon atoms, (2) a cycloaliphatic radical which contains from 4 to 18 carbon atoms, or (3) an araliphatic radical having from 6 to 18 carbon atoms in its aromatic portion, and from 3 to 30 carbon atoms in its aliphatic portion, or a combination of said compounds, with at least one mole of a tertiary amine having a $pk_a$ greater than 7 per equivalent of N-chloro amide, at a temperature from about 20° to about 180° C., in an inert solvent, to convert the N-chloro amide groups into isocyanate groups.

2. The process of claim 1 wherein an aliphatic compound containing from 1 to 3 N-chloro amide groups bound to from 1 to 3 secondary or tertiary carbon atoms, or a combination thereof, is utilized and the aliphatic portion of said compound contains from 3 to 30 carbon atoms.

3. The process of claim 1 wherein a cycloaliphatic compound containing from 1 to 3 N-chloro amide groups bound to from 1 to 3 secondary or tertiary carbon atoms, or a combination thereof, is utilized, and the cycloaliphatic portion of the compound contains from 4 to 18 carbon atoms.

4. The process of claim 1 wherein an araliphatic compound containing from 1 to 3 N-chloro amide groups bound to from 1 to 3 secondary or tertiary carbon atoms, or a combination thereof, is utilized, having from 6 to 18 carbon atoms in the aryl portion of said compound and from 3 to 30 carbon atoms in the aliphatic portion of said compound.

5. The process of claim 1, 2, 3 or 4, wherein the tertiary amine is selected from the group consisting a trimethyl amine, triethyl amine, tri-n-propyl amine, tri-n-butyl amine, and 2,4,6-trimethyl pyridine.

* * * * *